(12) United States Patent
Konya

(10) Patent No.: US 8,348,857 B2
(45) Date of Patent: Jan. 8, 2013

(54) LANCING SYSTEM

(75) Inventor: Ahmet Konya, Ludwigshafen (DE)

(73) Assignee: Roche Diagnostics Operations, Inc., Indianapolis, IN (US)

(*) Notice: Subject to any disclaimer, the term of this patent is extended or adjusted under 35 U.S.C. 154(b) by 0 days.

(21) Appl. No.: 13/210,626

(22) Filed: Aug. 16, 2011

(65) Prior Publication Data
US 2012/0041340 A1 Feb. 16, 2012

Related U.S. Application Data

(63) Continuation of application No. PCT/EP2010/000564, filed on Jan. 30, 2010.

(30) Foreign Application Priority Data
Feb. 16, 2009 (EP) ..................................... 09002121

(51) Int. Cl.
*A61B 5/00* (2006.01)
*A61B 17/32* (2006.01)
(52) U.S. Cl. ........................................ 600/583; 606/183
(58) Field of Classification Search .................. 600/583, 600/584; 606/181–183
See application file for complete search history.

(56) References Cited

U.S. PATENT DOCUMENTS
2004/0132167 A1   7/2004   Rule et al.

FOREIGN PATENT DOCUMENTS

| | | |
|---|---|---|
| EP | 0254203 A2 | 1/1988 |
| EP | 0931507 A1 | 7/1999 |
| EP | 1360935 A1 | 11/2003 |
| EP | 1598011 A2 | 11/2005 |
| EP | 2030566 A1 | 3/2009 |
| WO | 0040150 A1 | 7/2000 |
| WO | 2004041082 A1 | 5/2004 |
| WO | 2005107596 A2 | 11/2005 |
| WO | 2007041244 A2 | 4/2007 |
| WO | 2008131920 A2 | 11/2008 |

*Primary Examiner* — Brian Szmal
(74) *Attorney, Agent, or Firm* — Harness, Dickey

(57) ABSTRACT

The invention relates to a lancing system, comprising test elements, lancing elements, test elements each assigned to a lancing element and a hand-held device comprising a holder, which during a puncture holds a lancing element and a test element assigned to it, a lancing drive, which during a puncture moves the holder out of a starting position into a piercing position and back into the starting position, a light-sensitive sensor for analyzing a body fluid sample taken up by a test element, and a light source for illuminating the test element. According to the invention, the sensor is disposed in a housing, the outside of which the holder touches in the starting position.

18 Claims, 4 Drawing Sheets

LANCING SYSTEM

CROSS-REFERENCE TO RELATED APPLICATIONS

This application is a continuation of International Application No. PCT/EP2010/000564, filed on Jan. 30, 2010, which claims the benefit and priority of European Patent Application No. 09002121.3, filed on Feb. 16, 2009. The entire disclosures of the above applications are incorporated herein by reference.

BACKGROUND

The invention relates to a lancing system comprising lancing elements having test elements useful, for example, in obtaining and testing blood samples. Such lancing systems are required by diabetics, for example, who must check their blood sugar level several times a day and for this purpose require a body fluid sample, in general blood or interstitial fluid, obtained by a puncture wound generated with a lancing system.

Lancing systems in which one and the same device can be used for generating a puncture wound and for taking up a sample from a generated puncture wound provide particularly high user comfort. By automatically taking up the sample, it is made easier for the user to analyze a body fluid sample, which is an important advantage, notably for persons with limited manual mobility due to age or disease. Automatic sample collection additionally carries a lower risk of contaminating the sample, which could lead to a distortion of measurement results.

SUMMARY

With lancing systems of the type mentioned above, which analyze a body fluid sample using optical means, for example by photometric concentration measurement, light must be transmitted with minimized signal loss and maximized signal-to-noise ratio from a test element to a light-sensitive sensor. It is an object of the present invention to provide, in a cost-effective manner, a lancing system having lancing elements and test elements assigned to the lancing elements. In addition to lancing and test elements, such a system includes a hand-held device comprising a holder, which during a puncture holds a lancing element and a test element assigned to it, a lancing drive, which during a puncture moves the holder out of a starting position into a piercing position and back into the starting position, a light-sensitive sensor for analyzing a body fluid sample taken up by a test element, and a light source for illuminating the test element.

In a lancing system according to the invention, the light-sensitive sensor is disposed in a housing, the outside of which the holder touches in the starting position. According to the invention, thereby precise positioning of the test element relative to the sensor can be achieved using simple means, so that measurements can be carried out with advantageously low sample volumes and an accordingly small surface area of the test element to be evaluated. The housing can notably shield interfering light, so that measurement light can be transferred from the test element to the sensor with low signal losses and a good signal-to-noise ratio.

With the lancing system according to the invention, it is possible to use lancing elements that are designed integral with test elements, as is described in EP 1 360 935 B1, for example. Such lancing elements typically have a capillary channel, which leads to a test element, for example a glued-on test field containing detection reagents, disposed on a body of the lancing element. However, it is also possible to use separate lancing elements and test elements, which are joined by a suitable transport mechanism in the lancing device, in particular in the holder, so that after a puncture a lancing element can take up a body fluid sample and transfer it to a test element. Such a system is described in WO 2005/107596 A2, for example.

According to an advantageous refinement of the invention, the housing comprises, on the outside thereof, a guide that guides the holder during a puncture movement. In this way, in the starting position the holder assumes a predefined position relative to the housing, and thus relative to the sensor disposed in the housing, in a manner that can always be reproduced and is highly accurate. This has the advantage that a test element held by the holder likewise assumes a defined starting position for a measurement with high precision and, as a result, the region captured by the sensor can be limited to an advantageously small surface area. This is an important advantage, notably for measurements with small samples volumes, because small sample volumes can wet only small surface areas and the signal-to-noise ratio generally improves as the agreement of the region captured by the sensor with the surface area of the test element relevant for the measurement increases. The guide is preferably a linear guide, for example a dovetail guide or rail guide.

According to a further advantageous refinement of the invention, the light source for illuminating the test element is disposed in the housing. In this way, interfering influence of the measurement by ambient light can be largely avoided, because substantially the entire beam path from the light source to the test element and from the test element to the sensor can be shielded in the housing. In principle, however, it is also possible to dispose the light source outside of the housing and to analyze a test element in transmissions, for example.

Preferably at least one optical element is disposed in the housing, for example one or more lenses and/or one or more minors. In this way, an optical beam path for precise measurement can be predefined in the housing, the beam path optimally utilizing the space available in the device.

The housing containing the sensor is preferably disposed in a stationary manner in the interior of the device. However, in principle it is also possible to dispose the sensor in a multipart housing, which comprises a housing part that moves together with the holder during a puncture.

DRAWINGS

Further details and advantages of the invention will be described based on an embodiment with reference to the attached drawings.

DETAILED DESCRIPTION

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom.

Figure 1:
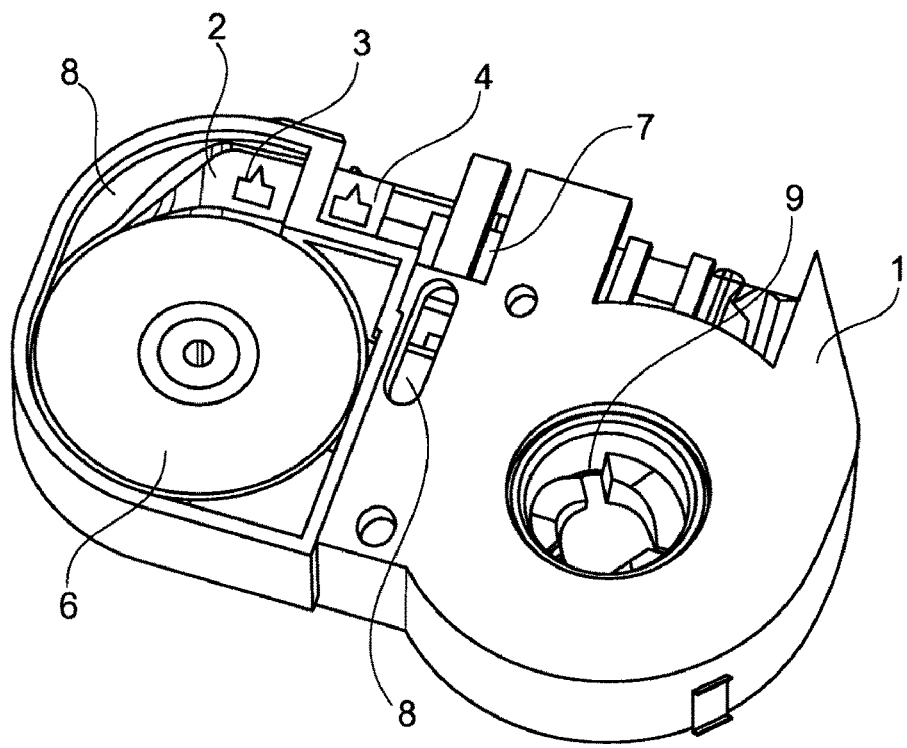
FIG. 1 is a schematic illustration of a lancing system according to the invention with an opened device housing.
Figure 2:
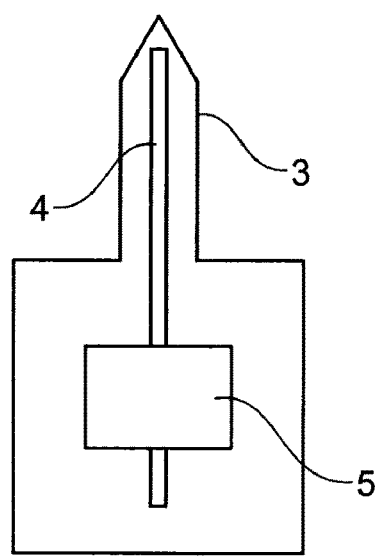
FIG. 2 is a schematic illustration of a lancing element comprising a test element.

FIG. 1 shows an embodiment of a lancing system 1 with an opened device housing. A carrier tape 2 carrying lancing and test elements is disposed in the device housing. Each of the lancing elements 3 shown by way of example in FIG. 2 has a channel 4 for transporting body fluid to a test element 5 containing detection reagents for the photometric determination of an analyte concentration.

The carrier tape 2 is wound with unused lancing and test elements to form a roll 6 and is guided from there to the holder 7, which during a puncture holds a lancing element 3 with the associated test element 5. The holder 7 is coupled to a lancing drive 8, which during a puncture moves the holder 7 from a starting position into a piercing position, which constitutes the point of reversal of a puncture and return movement, and back into the starting position.

The carrier tape 2 can be wound with used lancing and test elements by means of a winding unit 9. This winding process causes tape to be transported, so that unused lancing and test elements can be guided consecutively to the holder 7.

Figure 3:
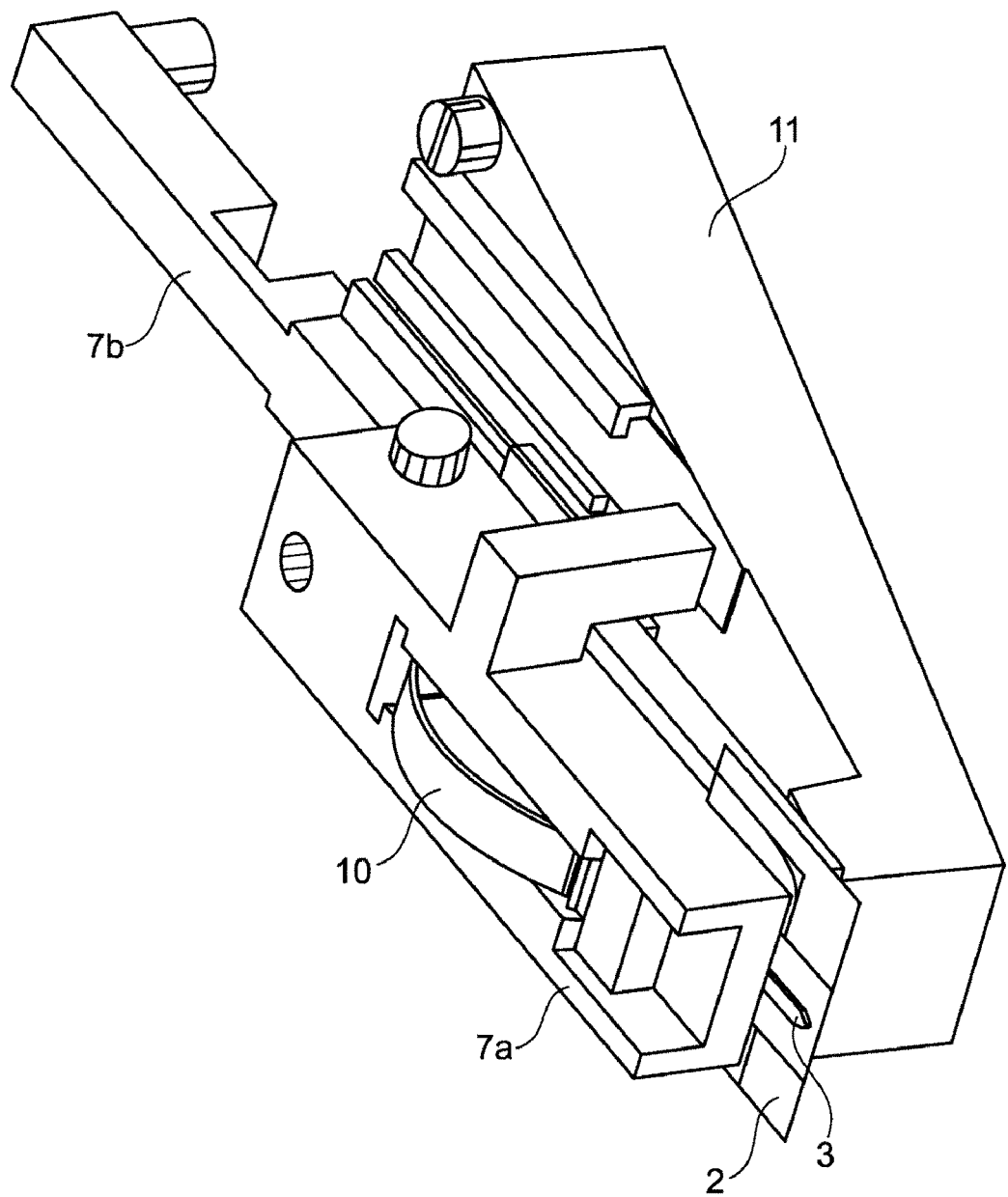
FIG. 3 shows the holder of the illustrated lancing system comprising a lancing element and a housing, in which a sensor is disposed.

FIG. 3 shows a detailed view of the holder 7 comprising a lancing element 3 on a section of the carrier tape 2. The holder is composed of two holding elements 7a, 7b, which can be pivoted relative to one another and which during a puncture clamp a lancing element 3, comprising a test element 5 associated therewith, between each other. So as to enable tape to be transported, the two holding elements 7a, 7b can be pivoted with respect to one another about an axis, whereby a gap opens between them. When a new lancing element 3 with an associated test element has been moved into the usage position, the gap is closed again by a corresponding movement of the two holding elements 7a, 7b. The closing motion is caused by the restoring force of a spring 10.

Figure 4:
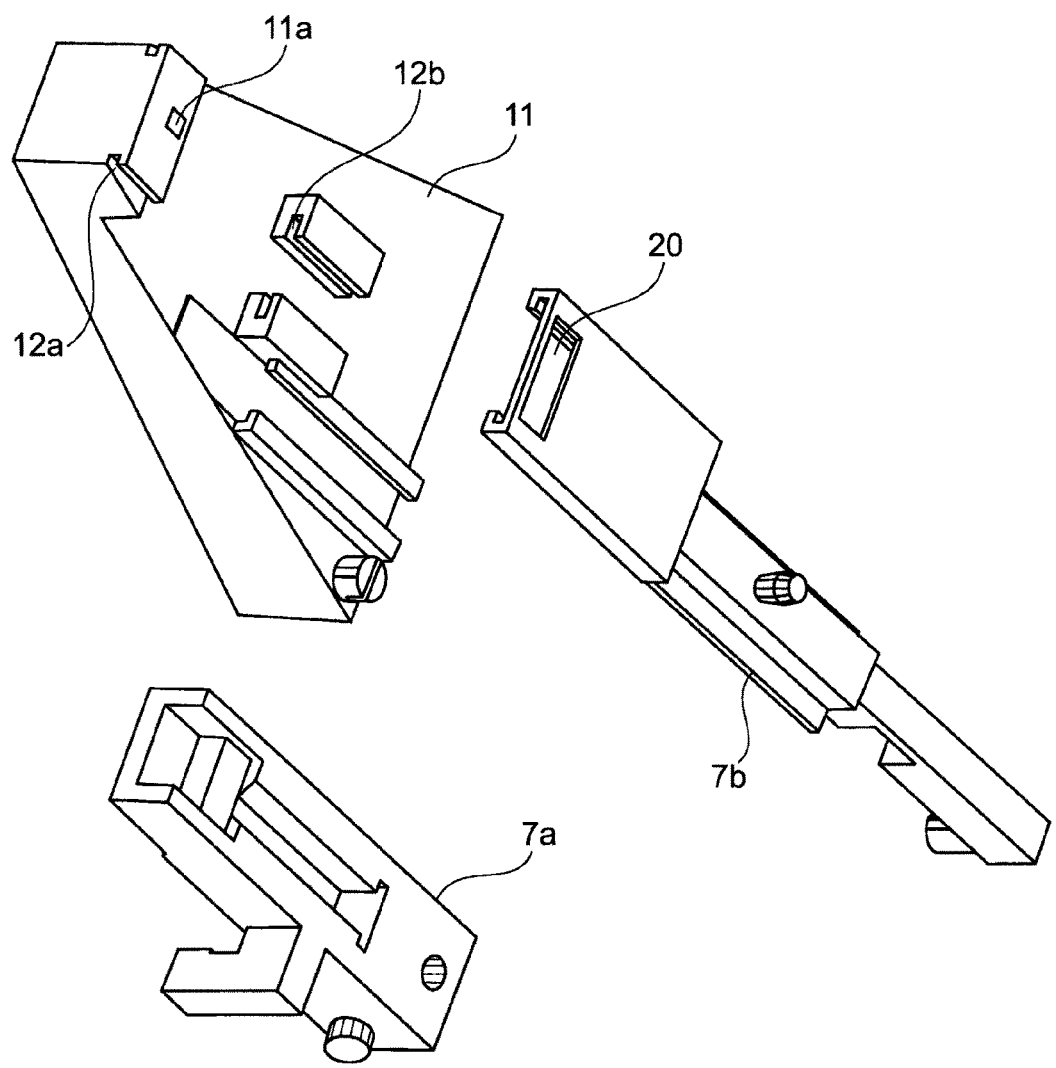
FIG. 4 is an exploded view of FIG. 3.
Figure 5:
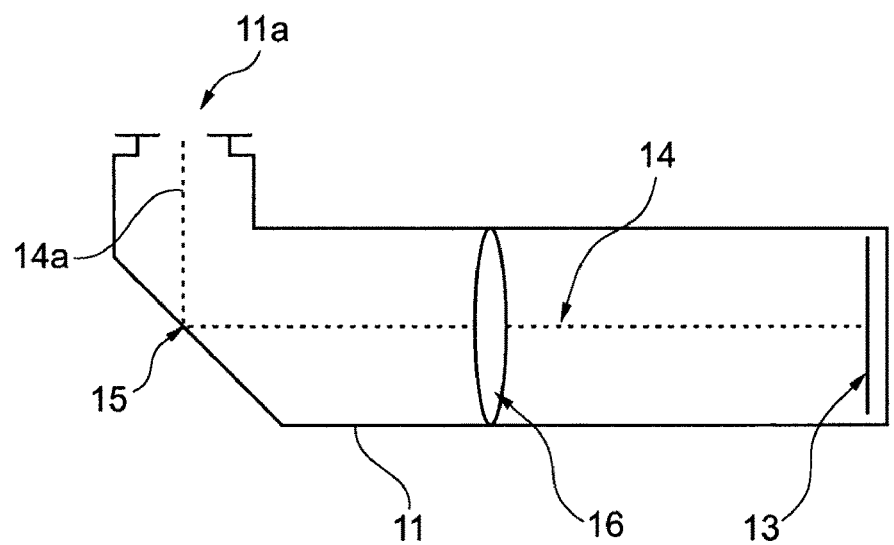
FIG. 5 is a sectional view of the housing containing the sensor.

In the starting position shown in FIG. 3, the holder 7 is seated against the outside of a housing 11, in which a light-sensitive sensor 13 for analyzing a body fluid sample taken up by a test element 5 is disposed. A sectional view of the housing 11 is shown in FIG. 5. The housing 11 has a window 11a, through which light travels from the test element 5 to the sensor 13. This window 11a is preferably designed as an opening in the housing 11. However, it is also possible to design the window 11a as a transparent housing section. The holding element 7b seated against the housing 11 likewise has a window 20, which is shown in FIG. 4. The window 20 is preferably a cut-out and can advantageously be designed larger than the window 11a, with which it is aligned in the starting position of the holder 7.

The opaque housing 11 shields interfering light, so that measurements can be carried out with a good signal-to-noise ratio. On the outside, the housing 11 comprises guides 12a, 12b, which in the embodiment shown are grooves or dovetail guides, which guide the holder 7 during a puncture movement. In this way, a rectilinear and therefore low-pain puncture movement is brought about, and advantageously the position of the test element 5 in the starting position of the holder 7 relative to the housing 11, and thus relative to the sensor 13 disposed therein, is very precisely predefined.

The sensor 13 disposed in the housing 11 and a related beam path 14 comprising optical elements 15, 16, which in FIG. 5 are shown schematically as a minor 15 and a lens 16, can therefore be matched during production very precisely to the position of a test element 5 that is held by the holder 7 in the starting position and contains a taken-up body fluid sample, so that precise measurement is possible even with very small sample volumes of just a few nl, for example 20 nl to 200 nl.

Figure 6:
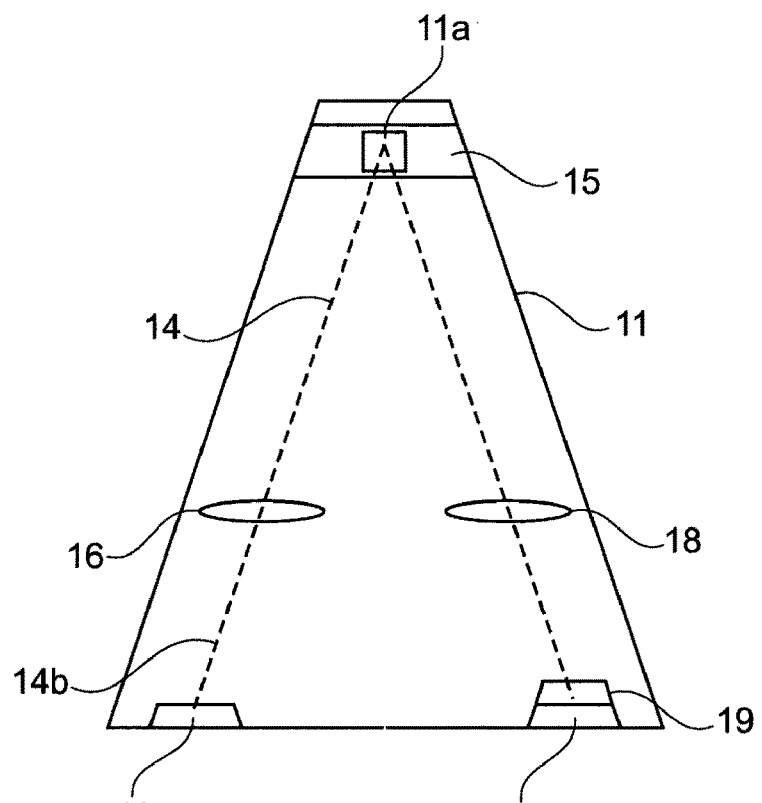
FIG. 6 is a further sectional view of the housing containing the sensor.

In the housing, which is tapering in a V shape in the puncture direction, a light source 17 for illuminating the test element 5, for example a LED, is arranged, as is shown in FIG. 6 in a schematic view. The light emitted by the light source 17 is directed via optical elements, for example a lens 18, an aperture 19 and the mirror 15, to the test element and from there on a V-shaped beam path to the sensor 13, as is indicated in FIG. 6.

The beam path 14 runs at an angle in the housing 11. A starting section 14a of the beam path originating at the test element 5 to be analyzed runs transversely to the puncture direction, preferably perpendicularly to the puncture direction, in which the holder 7 is moved during a puncture. An end section 14b of the beam path 14 runs along the puncture direction and preferably forms an acute angle therewith.

REFERENCE NUMERALS

1 Lancing system
2 Carrier tape
3 Lancing element
4 Channel
5 Test element
6 Roll
7 Holder
7a Holding element
7b Holding element
8 Lancing drive
9 Winding unit
10 Spring
11 Housing
11a Window
12
12a Guides
12b Guides
13 Sensor
14 Beam path
14a Starting section
14b End section
15 Mirror
16 Lens
17 Light source
18 Lens
19 Aperture
20 Window

What is claimed is:
1. A lancing system, comprising
a plurality of lancing elements,
a plurality of test elements, each of which is assigned to a lancing element,
a hand-held device, comprising a holder that is configured to hold a lancing element of the plurality of lancing elements and a correspondingly assigned test element, a lancing drive that is configured to move the holder out of a starting position into a piercing position and back into the starting position, a light-sensitive sensor that is configured to analyze a body fluid sample taken up by a test element, and a light source for illuminating the test element, and
a housing, distinct from the holder, wherein the holder is seated against an outside of the housing, wherein the sensor is disposed in the housing.

2. The lancing system according to claim 1, wherein the housing comprises on an outside at least one guide, that is configured to guide the holder during a puncture movement.

3. The lancing system according to claim 1, wherein at least one lens is disposed in the housing.

4. The lancing system according to claim 1, wherein at least one mirror is disposed in the housing.

5. The lancing system according to claim 1, wherein the housing comprises a window, which a test element of the plurality of test elements, held by the holder touches when the holder is in the starting position.

6. The lancing system according to claim 1, wherein an angled beam path runs in the housing.

7. The lancing system according to claim 1, wherein the test element is a test field containing detection reagents for photometric concentration determination.

8. The lancing system according to claim 1, wherein the lancing elements have a base body, which carries the correspondingly assigned test element.

9. The lancing system according to claim 1, wherein the light source is positioned at a location in the housing such that a starting section of a beam path originating from the test element to be analyzed runs in the housing transversely to the puncture direction in which the holder is moved during a puncture.

10. The lancing system according to claim 1, wherein the light source is positioned at a location in the housing such that an end section of a beam path originating from the test element to be analyzed runs in the housing along the puncture direction in which the holder is moved during a puncture.

11. The lancing system according to claim 1, wherein the housing shields a beam path which leads from the test element to the sensor, from interfering light.

12. The lancing system according to claim 1, wherein the light source is disposed in the housing.

13. The lancing system according to claim 1, further comprising a carrier tape which carries the lancing elements.

14. The lancing system according to claim 1, wherein the holder comprises two holding elements that are configured to be moved relative to one another, between which a lancing element of the plurality of lancing elements is held.

15. The lancing system according to claim 1, wherein the housing is tapered in the puncture direction.

16. A lancing system, comprising:
   a plurality of test elements each having a corresponding lancing element;
   a housing having an outer surface and defining an inner enclosure;
   a light-sensitive sensor disposed within the inner enclosure of the housing; and
   a holder seated against the outer surface of the housing and collectively comprising a first holding element and a second holding element movably connected to each other, the holder configured to hold a testing element of the plurality of test elements.

17. The lancing system of claim 16, wherein the outer surface of the housing further comprises a guide that slidably captures at least one of the first and second holding elements against the housing.

18. The lancing system of claim 16, wherein the housing defines a window therethrough, wherein the holder is configured to position a test element of the test elements against the window in a starting position.

* * * * *